(12) United States Patent
Foster et al.

(10) Patent No.: US 10,279,169 B2
(45) Date of Patent: May 7, 2019

(54) TORQUE TOOL FOR FIXABLE STIMULATION-SENSING LEADS

(71) Applicant: Cardiac Pacemakers, Inc., St. Paul, MN (US)

(72) Inventors: Arthur J. Foster, Blaine, MN (US); Linda L. Evert, Circle Pines, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 369 days.

(21) Appl. No.: 15/098,304

(22) Filed: Apr. 13, 2016

(65) Prior Publication Data
US 2016/0303367 A1    Oct. 20, 2016

Related U.S. Application Data

(60) Provisional application No. 62/147,501, filed on Apr. 14, 2015.

(51) Int. Cl.
*A61N 1/05* (2006.01)
*A61B 17/28* (2006.01)
*A61B 17/00* (2006.01)

(52) U.S. Cl.
CPC .......... *A61N 1/057* (2013.01); *A61B 17/2812* (2013.01); *A61B 2017/00469* (2013.01); *A61N 2001/058* (2013.01)

(58) Field of Classification Search
CPC .... A61N 1/06; A61N 1/057; A61N 2001/058; A61N 1/05; A61B 17/2812; A61B 2017/00469; A61B 17/28; A61B 17/29
See application file for complete search history.

(56) References Cited

U.S. PATENT DOCUMENTS

| | | | |
|---|---|---|---|
| 4,616,651 A | * | 10/1986 | Golden ................ A61B 17/128 606/142 |
| 4,813,107 A | | 3/1989 | Cetrone |
| 5,454,818 A | | 10/1995 | Hambleton et al. |
| 5,741,321 A | | 4/1998 | Brennen |
| 7,512,446 B2 | | 3/2009 | Honeck |
| 8,170,692 B2 | | 5/2012 | Truong et al. |
| 8,747,417 B2 | | 6/2014 | Truong |
| 2006/0161182 A1 | | 7/2006 | Vandenbroek |

(Continued)

OTHER PUBLICATIONS

Shore D Hardness Test (Durometer Scale)—Hardness of Plastic Materials, 2018, Omnexus by SpecialChem, pp. 1-3.*

(Continued)

*Primary Examiner* — Christopher L Templeton
*Assistant Examiner* — George J Ulsh

(57) ABSTRACT

A fixation tool for applying torque to a terminal pin of an active fixation medical electrical lead includes a first handle, a second handle, an elastic member, a first jaw, a second jaw, and an insert. The insert is disposed at an end of the tool slot proximal to the elastic member. The insert includes an insert slot configured to align with the tool slot. The fixation tool is configured such that pressing the first handle and the second handle toward each other causes a movement of the first jaw and the second jaw relative to each other to change a width of the insert slot. The first jaw and the second jaw are comprised of a first material. The insert is comprised of a second material. The first material is harder than the second material.

6 Claims, 8 Drawing Sheets

(56) References Cited

U.S. PATENT DOCUMENTS

2009/0177196 A1    7/2009  Zlock et al.

OTHER PUBLICATIONS

International Preliminary Report on Patentability issued in PCT/US2016/027392, dated Oct. 26, 2017, 11 pages.
International Search Report and Written Opinion issued in PCT/US2016/027392 dated Aug. 16, 2016, 16 pages.
Invitation to Pay Additional Fees issued in PCT/US2016/027392, dated Jun. 20, 2016, 5 pages.

* cited by examiner

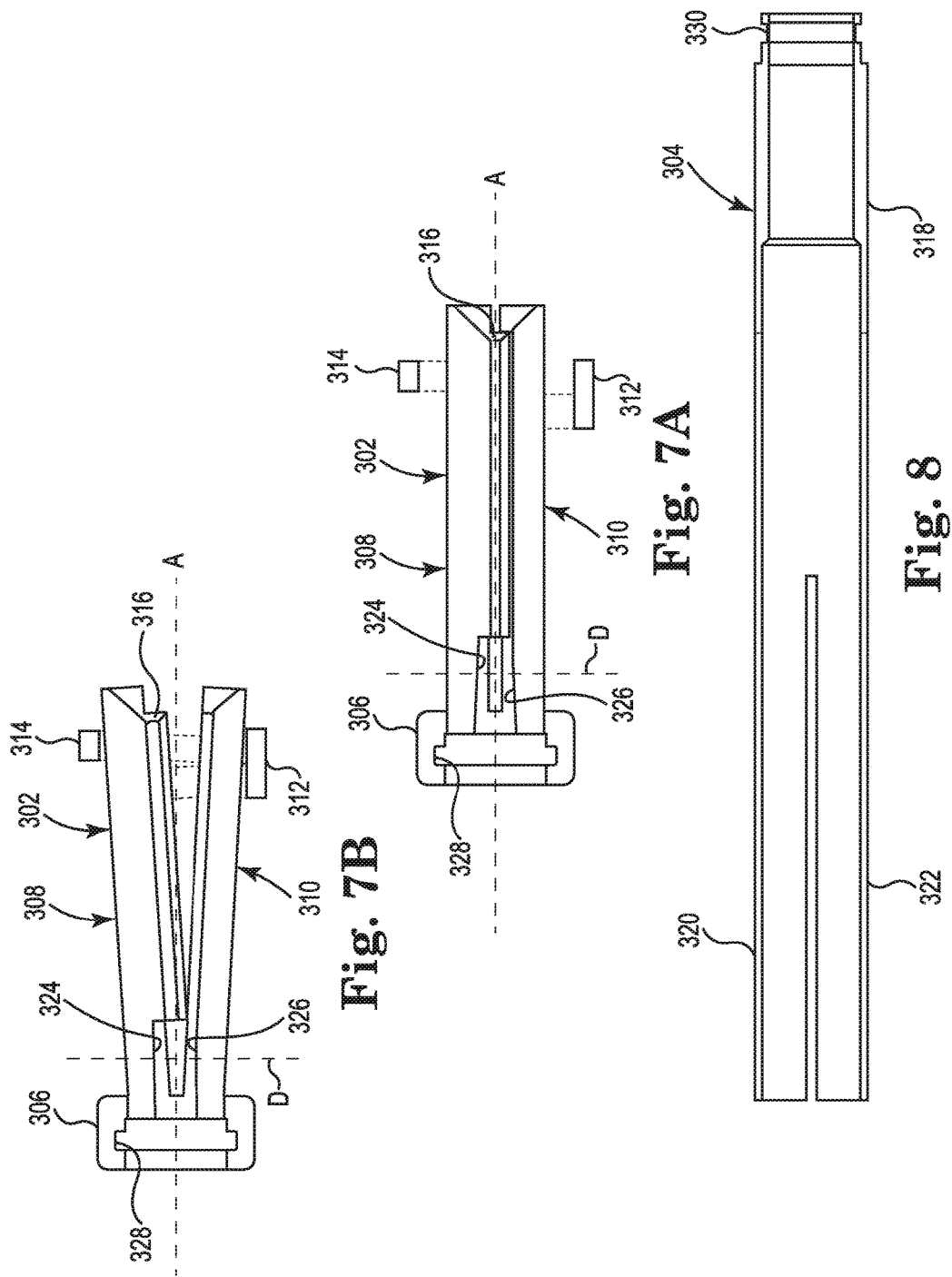

TORQUE TOOL FOR FIXABLE STIMULATION-SENSING LEADS

CROSS-REFERENCE TO RELATED APPLICATION

This application claims priority to Provisional Application No. 62/147,501, filed Apr. 14, 2015, which is herein incorporated by reference in its entirety.

TECHNICAL FIELD

The present invention relates to implantable medical device leads. More specifically, the invention relates to fixation tools for implanting active fixation medical electrical leads.

BACKGROUND

Implantable medical devices, such as cardiac rhythm management (CRM) devices and neuromodulation devices, are used in a variety of therapeutic applications. In some applications, one or more implantable electrical leads are employed to deliver therapy from an implanted medical device to tissues within a body. CRM systems may employ electrical leads implanted within a patient's heart. It is often the case that such leads are secured to a desired location in the heart by a mechanical device. Such mechanical fixation devices may include a corkscrew-shaped device known as a helix. The helix may be designed such that it is retracted into the lead during insertion and positioning within the heart. Once positioned, the helix is rotated to extend the helix and screw it into the heart muscle.

Helix rotation may be driven by torque applied to a terminal pin and transmitted through a conductor coil extending through the lead from the terminal pin to the helix. Terminal pins are often quite small and have smooth, cylindrical surfaces. This presents some difficulty in applying a desired amount of torque to ensure a number of rotations necessary to properly seat the helix. Fixation tools are often used to apply torque to the terminal pin. Improved fixation tools may more reliably apply torque to the terminal pin.

SUMMARY

In Example 1, a fixation tool for applying torque to a terminal pin of an active fixation medical electrical lead includes a first handle, a second handle, an elastic member connecting the first handle to the second handle, a first jaw, a second jaw, and in insert. The first jaw projects beyond the elastic member from the first handle. The second jaw projects beyond the elastic member from the second handle. The first jaw and the second jaw are spaced apart, forming a tool slot extending from ends of each of the first jaw and the second jaw distal from the elastic member and toward the elastic member. The insert is disposed at an end of the tool slot proximal to the elastic member. The insert includes an insert slot configured to align with the tool slot. The fixation tool is configured such that pressing the first handle and the second handle toward each other causes a movement of the first jaw and the second jaw relative to each other to change a width of the insert slot. The first jaw and the second jaw are comprised of a first material, the insert is comprised of a second material, and the first material is harder than the second material.

In Example 2, the tool of Example 1, wherein the first handle, the second handle, the elastic member, the first jaw and the second jaw are integrally formed.

In Example 3, the tool of any of Examples 1-2, wherein the second material has a Shore hardness of less than 90 D.

In Example 4, the tool of any of Examples 1-3, wherein the insert includes a plurality of structures projecting from a surface of the insert slot.

In Example 5, the tool of any of Examples 1-4, wherein the tool is configured such that pressing the first handle toward the second handle causes a movement of the first jaw and the second jaw away from each other, increasing a width of the insert slot from less than a diameter of the terminal pin to greater than the diameter of the terminal pin.

In Example 6, a fixation tool for applying torque to a terminal pin of an active fixation medical electrical lead includes a first handle, a second handle, an elastic member connecting the first handle to the second handle, a first jaw, a second jaw, and a lead support member. The first jaw projects beyond the elastic member from the first handle. The second jaw projects beyond the elastic member from the second handle. The first jaw and the second jaw are spaced apart, forming a tool slot extending from ends of each of the first jaw and the second jaw distal from the elastic member and toward the elastic member. The tool is configured such that pressing the first handle toward the second handle causes a movement of the first jaw and the second jaw relative to each other to change a width of the tool slot. The lead support member projects from at least one of the first jaw and the second jaw in a direction perpendicular to a plane containing the movement of the first jaw and the second jaw. The lead support member includes a cross-section forming at least a major arc of a circle and defining an axis. The axis is aligned with the tool slot.

In Example 7, the tool of Example 6, wherein the major arc is less than 220 degrees.

In Example 8, the tool of Example 6, wherein the lead support member has a cross-section forming a circle, and projects from the first jaw and is adjacent to the second jaw.

In Example 9, the tool of any of Examples 6-8, wherein the first handle, the second handle, the elastic member, the first jaw, and the second jaw are integrally formed; and the lead support member is bonded to at least one of the first jaw and the second jaw.

In Example 10, the tool of any of Examples 6-9, wherein the tool is configured such that pressing the first handle toward the second handle causes a movement of the first jaw and the second jaw away from each other, increasing a width of the tool slot from less than a diameter of the terminal pin to greater than the diameter of the terminal pin.

In Example 11, the tool of any of Examples 6-9, further comprising an insert disposed at an end of the tool slot proximal to the elastic member, the insert including an insert slot configured to align with the tool slot, wherein the first jaw and the second jaw are comprised of a first material, the insert is comprised of a second material, and the first material is harder than the second material, wherein the tool is configured such that pressing the first handle toward the second handle causes a movement of the first jaw and the second jaw away from each other, increasing a width of the insert slot from less than a diameter of the terminal pin to greater than the diameter of the terminal pin.

In Example 12, a fixation tool for applying torque to a terminal pin of an active fixation medical electrical lead having a terminal boot with a terminal boot seal includes a terminal pin member and a terminal boot member. The terminal pin member includes a first rotating joint member, a first jaw projecting from the first rotating joint member, and a second jaw projecting from the first rotating joint member. The first rotating joint member has a generally hollow cylindrical shape defining a tool axis. The first jaw includes a first inner surface. The first inner surface faces the tool axis and extends from proximate to the first rotating joint member to a distance distal from the first rotating joint member. The second jaw includes a second inner surface facing the tool axis and diametrically opposite of the first inner surface. The second inner surface extends from proximate to the first rotating joint member to the distance distal from the first rotating joint member. The first inner surface and the second inner surface are diametrically spaced from each other by a first width proximate to the first rotating joint member, and by a second width less than the first width at the distance distal from the first rotating joint member. Forcing the first jaw and the second jaw apart from each other moves the first inner surface and the second inner surface away from each other at the distance distal from the first rotating joint member to the first width. The terminal boot includes a second rotating joint member, a first leg projecting from the second rotating joint member, and a second leg projecting from the second rotating joint member and parallel to the first leg. The second rotation joint member has a generally hollow cylindrical shape. The second leg is spaced diametrically apart from the first leg by a third width. Pressing the first leg and the second leg together spaces the second leg diametrically apart from the first leg by a fourth width that is less than the third width. The first rotating joint member is connected to the second rotating joint member such that the terminal pin member and the terminal boot member may rotate freely relative to each other.

In Example 13, the tool of Example 12, wherein the terminal pin member further includes a first tab connected to the first jaw, and a second tab connected to the second jaw. The first tab extends around the second jaw. The first tab is distal from the first rotating member. The second tab extends around the first jaw. The second tab is distal from the first rotating member. Pressing the first tab and the second tab toward each other forces the first jaw and the second jaw apart from each other.

In Example 14, the tool of any of Examples 12-13, wherein the terminal pin member further includes a stylet funnel extending along at least a portion of the first jaw.

In Example 15, the tool of any of Examples 12-14, wherein the wherein the first rotating joint member and the second rotating joint member are connected to each other by a C-clip.

In Example 16, a fixation tool for applying torque to a terminal pin of an active fixation medical electrical lead includes a first handle, a second handle, an elastic member connecting the first handle to the second handle, a first jaw, a second jaw, and in insert. The first jaw projects beyond the elastic member from the first handle. The second jaw projects beyond the elastic member from the second handle. The first jaw and the second jaw are spaced apart, forming a tool slot extending from ends of each of the first jaw and the second jaw distal from the elastic member and toward the elastic member. The insert is disposed at an end of the tool slot proximal to the elastic member. The insert includes an insert slot configured to align with the tool slot. The tool is configured such that pressing the first handle and the second handle toward each other causes a movement of the first jaw and the second jaw relative to each other to change a width of the insert slot. The first jaw and the second jaw are comprised of a first material, the insert is comprised of a second material, and the first material is harder than the second material.

In Example 17, the tool of Example 16, wherein the first handle, the second handle, the elastic member, the first jaw and the second jaw are integrally formed.

In Example 18, the tool of any of Examples 16-17, wherein the insert is disposed in the tool by insert molding.

In Example 19, the tool of any of Examples 16-18, wherein the second material has a Shore hardness of less than 90 D.

In Example 20, the tool of any of Examples 16-17, wherein the second material is silicone rubber and the insert is glued to the first jaw and the second jaw.

In Example 21, the tool of any of Examples 16-20, wherein the insert includes a plurality of structures projecting from a surface of the insert slot.

In Example 22, the tool of any of Examples 16-21, wherein the tool is configured such that pressing the first handle toward the second handle causes a movement of the first jaw and the second jaw away from each other, increasing a width of the insert slot from less than a diameter of the terminal pin to greater than the diameter of the terminal pin.

In Example 23, a fixation tool for applying torque to a terminal pin of an active fixation medical electrical lead includes a first handle, a second handle, an elastic member connecting the first handle to the second handle, a first jaw, a second jaw, and a lead support member. The first jaw projects beyond the elastic member from the first handle. The second jaw projects beyond the elastic member from the second handle. The first jaw and the second jaw are spaced apart, forming a tool slot extending from ends of each of the first jaw and the second jaw distal from the elastic member and toward the elastic member. The tool is configured such that pressing the first handle toward the second handle causes a movement of the first jaw and the second jaw relative to each other to change a width of the tool slot. The lead support member projects from at least one of the first jaw and the second jaw in a direction perpendicular to a plane containing the movement of the first jaw and the second jaw. The lead support member includes a cross-section forming at least a major arc of a circle and defining an axis. The axis is aligned with the tool slot.

In Example 24, the tool of Example 23, wherein the lead support member projects from the first jaw and is adjacent to the second jaw.

In Example 25, the tool of Example 23, wherein the lead support member projects from the first jaw and the second jaw.

In Example 26, the tool of any of Examples 23-25, wherein the major arc is less than 220 degrees.

In Example 27, the tool of Example 23, wherein the lead support member has a cross-section forming a circle, and projects from the first jaw and is adjacent to the second jaw.

In Example 28, the tool of any of Examples 23-27, wherein the first handle, the second handle, the elastic member, the first jaw, the second jaw and the lead support member are integrally formed.

In Example 29, the tool of any of Examples 23-27, wherein the first handle, the second handle, the elastic member, the first jaw, and the second jaw are integrally formed; and the lead support member is bonded to at least one of the first jaw and the second jaw.

In Example 30, the tool of any of Examples 23-29, wherein the tool is configured such that pressing the first handle toward the second handle causes a movement of the first jaw and the second jaw away from each other, increasing a width of the tool slot from less than a diameter of the terminal pin to greater than the diameter of the terminal pin.

In Example 31, the tool of any of Examples 23-29, further comprising an insert disposed at an end of the tool slot proximal to the elastic member, the insert including an insert slot configured to align with the tool slot, wherein the first jaw and the second jaw are comprised of a first material, the insert is comprised of a second material, and the first material is harder than the second material, wherein the tool is configured such that pressing the first handle toward the second handle causes a movement of the first jaw and the second jaw away from each other, increasing a width of the insert slot from less than a diameter of the terminal pin to greater than the diameter of the terminal pin.

In Example 32, a fixation tool for applying torque to a terminal pin of an active fixation medical electrical lead having a terminal boot with a terminal boot seal includes a terminal pin member and a terminal boot member. The terminal pin member includes a first rotating joint member, a first jaw projecting from the first rotating joint member, and a second jaw projecting from the first rotating joint member. The first rotating joint member has a generally hollow cylindrical shape defining a tool axis. The first jaw includes a first inner surface. The first inner surface faces the tool axis and extends from proximate to the first rotating joint member to a distance distal from the first rotating joint member. The second jaw includes a second inner surface facing the tool axis and diametrically opposite of the first inner surface. The second inner surface extends from proximate to the first rotating joint member to the distance distal from the first rotating joint member. The first inner surface and the second inner surface are diametrically spaced from each other by a first width proximate to the first rotating joint member, and by a second width less than the first width at the distance distal from the first rotating joint member. Forcing the first jaw and the second jaw apart from each other moves the first inner surface and the second inner surface away from each other at the distance distal from the first rotating joint member to the first width. The terminal boot includes a second rotating joint member, a first leg projecting from the second rotating joint member, and a second leg projecting from the second rotating joint member and parallel to the first leg. The second rotation joint member has a generally hollow cylindrical shape. The second leg is spaced diametrically apart from the first leg by a third width. Pressing the first leg and the second leg together spaces the second leg diametrically apart from the first leg by a fourth width that is less than the third width. The first rotating joint member is connected to the second rotating joint member such that the terminal pin member and the terminal boot member may rotate freely relative to each other.

In Example 33, the tool of Example 32, wherein the terminal pin member further includes a first tab connected to the first jaw, and a second tab connected to the second jaw. The first tab extends around the second jaw. The first tab is distal from the first rotating member. The second tab extends around the first jaw. The second tab is distal from the first rotating member. Pressing the first tab and the second tab toward each other forces the first jaw and the second jaw apart from each other.

In Example 34, the tool of any of Examples 32-33, wherein the terminal pin member further includes a stylet funnel extending along at least a portion of the first jaw.

In Example 35, the tool of any of Examples 32-34, wherein the first rotating joint member and the second rotating joint member are connected to each other by a C-clip.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIGS. 7A and 7B are side cross-sectional views of member of the fixation tool of FIG. 5.

FIG. 8 is a side cross-sectional view of another member of the fixation tool of FIG. 5.

Figure 1:
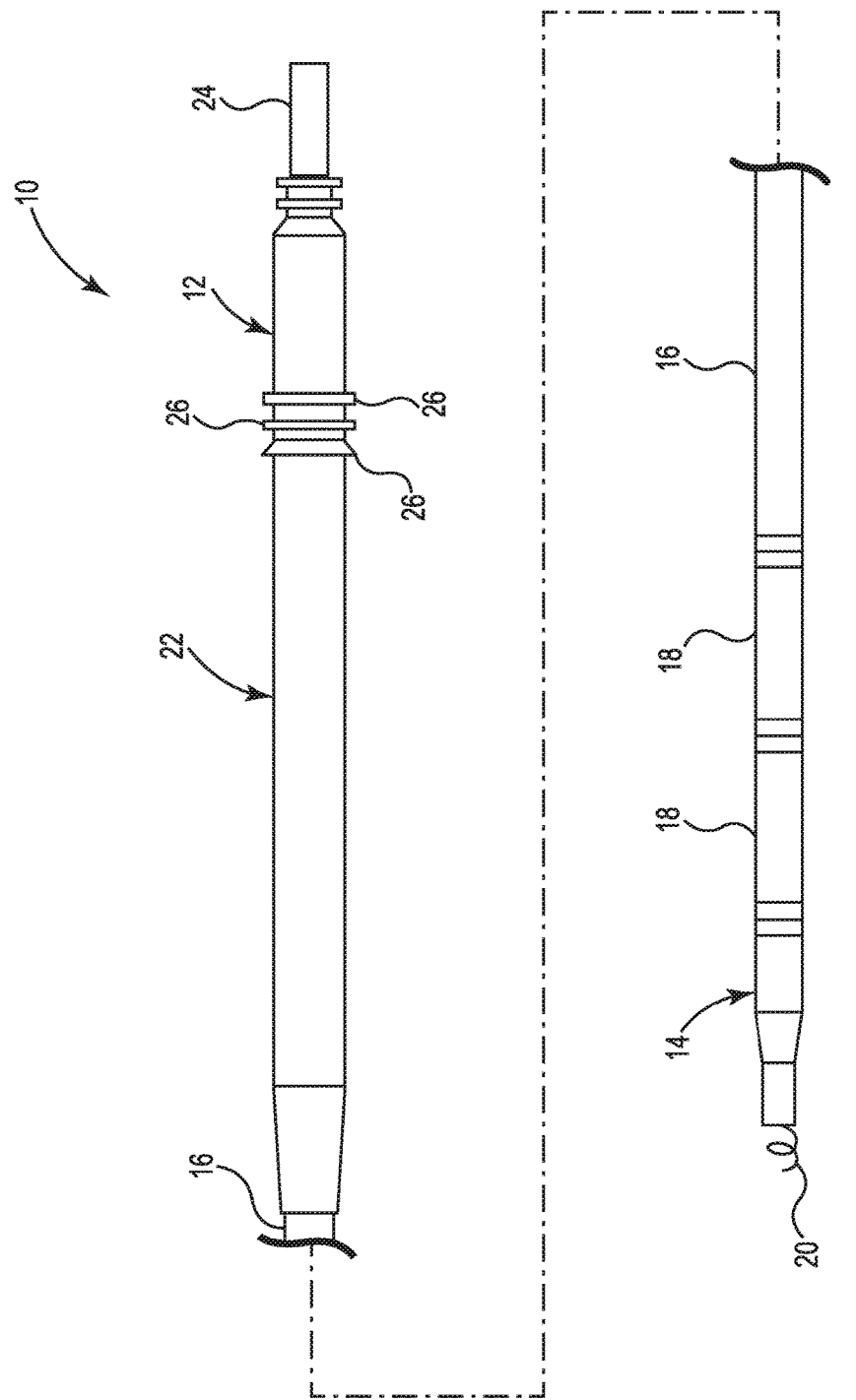
FIG. 1 is a side view of an active fixation lead.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a side view of an active fixation lead 10 for which fixation tool embodiments as described below may be employed. In some embodiments, the lead 10 extends from a proximal end 12 to a distal end 14. The lead 10 may include a lead body 16 extending generally from the proximal end 12 to the distal end 14. The lead body 16 may be a tubular structure including one or more lumens (not shown). The distal end 14, may include at least one electrode 18 (two shown) and a helix 20. The electrodes 18 may be employed to electrically couple the lead 10 with a heart (not shown). The helix 20 may be extended as shown in FIG. 1, to anchor the distal end 14 in the heart. The helix 20 may also be used to electrically couple the lead 10 with the heart.

The proximal end 12 may include a terminal boot 22 and a terminal pin 24. The terminal boot 22 may be made of an elastic polymer and may include one or more larger diameter terminal boot seals 26 (3 shown) for sealing the terminal boot 22 to an implantable electrical device (not shown). Terminal pin 24 may be a metallic cylinder having a relatively smooth surface for electrically connecting the lead 10 to the implanted medical device. At least one electrical conductor (not shown) may be disposed within the lumen within the lead body 16 and extend from the terminal pin 24 to the helix 20 to provide both a physical connection and, in some embodiments, an electrical connection between the terminal pin 24 and the helix 20. The electrical conductor may be in the form of a coil. In some embodiments, sensitive connections between the terminal pin 24 and the electrical conductor coil are contained within, and protected by, the terminal boot 22. The terminal pin 24 may rotate freely relative to the terminal boot 22 and the lead body 16 to transmit torque to the helix 20 by way of the connecting electrical conductor coil. In some embodiments, the terminal pin 24 may also include an aperture (not shown) extending axially through the terminal pin 24. The electrical conductor coil may also define a lumen (not shown) in communication with the aperture such that a stylet (not shown) may be inserted from the proximal end 12 to the distal end 14 to assist in positioning the distal end 14 and the helix 20 within the heart.

Torque may be applied to the terminal pin 24 to rotate the helix 20 and anchor the distal end 14 in the heart. For each type of the lead 10, a number of rotations of the terminal pin 24, and a corresponding number of rotations of the helix 20, are necessary to successfully anchor the distal end 14. A fixation tool is often employed to grip the terminal pin 24 and rotate it, while the number of rotations is counted to determine when the helix 20 is successfully implanted.

Figure 2A:
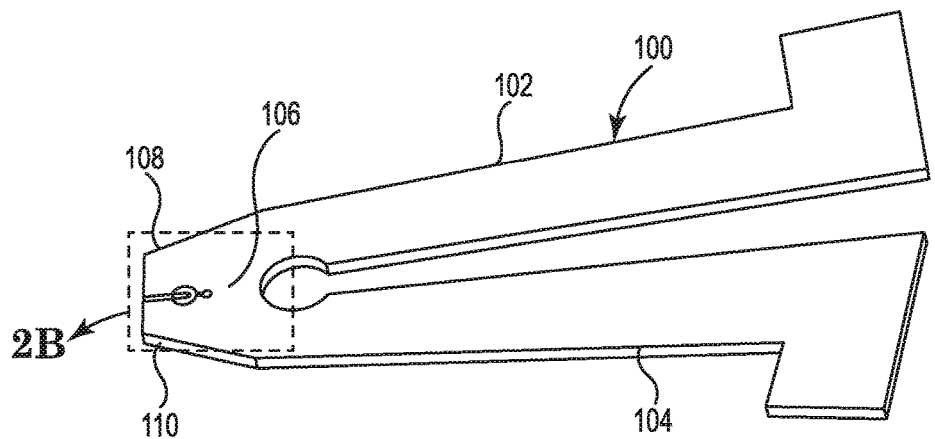
FIGS. 2A and 2B are perspective views of an exemplary fixation tool.
Figure 2B:
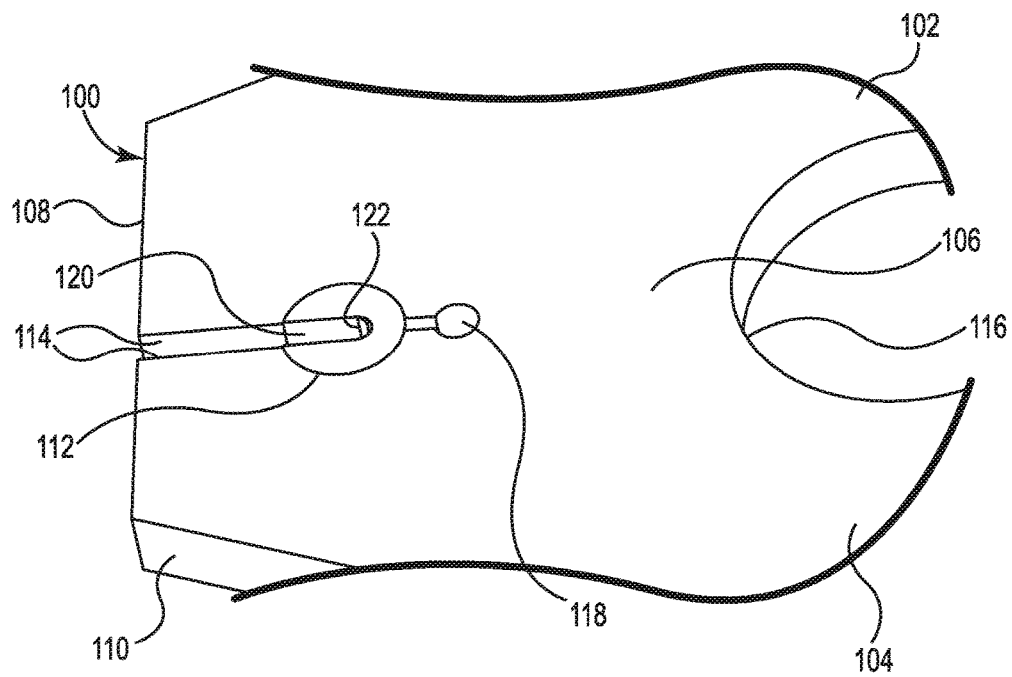

FIGS. 2A and 2B are perspective views of an exemplary fixation tool 100. FIG. 2B is an enlarged view of a portion of FIG. 2A. Fixation tool 100 may include a first handle 102, a second handle 104, an elastic member 106, a first jaw 108, a second jaw 110, and an insert 112. As shown in the embodiment in FIGS. 2A and 2B, the first handle 102, the second handle 104, the elastic member 106, the first jaw 108, and the second jaw 110 may be integrally formed of a first material. In other embodiments, elastic member 106 may be formed of a different material having greater elasticity than the first material. The first jaw 108 may project beyond the elastic member 106 from the first handle 102. The second jaw 110 may project beyond the elastic member 106 from the second handle 104. As shown in FIG. 2B, the first jaw 108 and the second jaw 110 are spaced apart, forming a tool slot 114. Tool slot 114 extends from ends of each of the first jaw 108 and the second jaw 110 distal from the elastic member 106 and toward the elastic member 106. Elastic member 106 may be a portion of the first material connecting the first handle 102 to the second handle 104 and may include a handle stress relieving element 116 and a jaw stress relieving element 118. The handle stress relieving element 116 may be a curved feature formed where the first handle 102 and the second handle 104 connect to the elastic element 106 to reduce a concentration of stress in the elastic member 106. The jaw stress relieving element 118 may also be a curved feature formed where the first jaw 108 projects from the first handle 102 and the second jaw 110 projects from the second handle 104 to reduce a concentration of stress in the elastic member 106.

As shown in FIG. 2B, the insert 112 may be disposed at or near an end of the tool slot 114 proximal to the elastic member 106 and the jaw stress relieving element 118. The insert 112 may include an insert slot 120. The insert slot 120 is configured to align with the tool slot 114. The insert 112 may be disposed in the tool 100 by insert molding. That is, the insert 112 is placed in a mold, and the rest of tool 100 is injection molded around the insert 112. Alternatively, the insert 112 may be glued to the first jaw 108 and the second jaw 110.

The tool slot 114 may be configured such that pressing the first handle 102 toward the second handle 104 causes a movement of the first jaw 108 and the second jaw 110 relative to each other to change a width of the insert slot 120. In the embodiment shown in FIGS. 2A and 2B, the tool slot 114 is configured such that pressing the first handle 102 toward the second handle 104 causes the first jaw 108 and the second jaw 110 to move farther from each other and against a restoring force of the elastic element 106. In doing so, the width of the tool slot 114 and the width of the insert slot 120 increase. In some embodiments, the width of the insert slot 120 increases from less than a diameter of the terminal pin 24 to a width greater than the diameter of the terminal pin 24.

As noted above, the first jaw 108 and the second jaw 110 are made of the first material. The insert slot 120 may be made of a second material. The first material is harder than the second material. For example, the first material may be a thermoplastic of relative high durometer, such as a polycarbonate or acrylonitrile butadiene styrene (ABS) having a Shore hardness of greater than 90 D. The second material may be a thermoplastic, thermoset, or cast material with a Shore hardness less than 90 D. The second material may be, for example, silicone rubber with a Shore hardness less than 90 D.

Considering FIGS. 1, 2A, and 2B together, the fixation tool 100 may be employed to apply torque to the terminal pin 24. The first handle 102 and the second handle 104 may be pressed toward each other. Movement of the first handle 102 and the second handle 104 works against the restoring force of the elastic member 106 moving the first jaw 108 and the second jaw 110 apart, increasing the width of the tool slot 114 and the insert slot 120 from less than the diameter of the terminal pin 24 to greater than the diameter of the terminal pin 24. Once the tool slot 114 and the insert slot 120 have a width greater than the diameter of the terminal pin 24, the terminal pin 24 may be slid into and along the tool slot 114 and into the insert slot 120. Releasing the first handle 102 and the second handle 104 allows the restoring force of the elastic member 106 to move the first jaw 108 and the second jaw 110 closer together, decreasing the width of the insert slot 120 to approximately the diameter of the terminal pin 24. Because the width of the insert slot 120 cannot return to the original width of less than the diameter of the terminal pin 24 due to the presence of the terminal pin 24, sufficient restoring force of the elastic member 106 remains to secure the fixation tool 100 to the terminal pin 24. Once secured to the terminal pin 24, the fixation tool 100 may be employed to apply torque to the terminal pin 24.

Securing the fixation tool 100 to the terminal pin 24 may be enhanced by the lower hardness of the second material comprising the insert 112. The second material may grip the terminal pin 24 more effectively than, for example, the harder first material, because it may deform against the terminal pin 24 to a greater extent, thereby increasing a surface contact area between the terminal pin 24 and the fixation tool 100. The second material may also have a greater coefficient of friction than the first material. These features may provide for a more secure mechanical connection between the fixation tool 100 and the terminal pin 24. Fixation tools without the insert 112 lack these features because they must rely on the harder first material of the first jaw 108 and the second jaw 110 lining the tool slot 114 to grip the terminal pin 24. By providing a more secure mechanical connection, the fixation tool 100 may be less likely to slip against the terminal pin 24, resulting in a more accurate count of the number of rotations of the terminal pin 24, and a more successful implantation of the helix 20. A more secure mechanical connection may be particularly beneficial during the implantation process when fluids may be present on the surface of the terminal pin 24.

As shown in FIG. 2B, in some embodiments, the insert 112 may include a plurality of structures 122 projecting from a surface of the insert slot 120. The plurality of structures 122 projecting from the surface of the insert slot 120 may further enhance securing the fixation tool 100 to the terminal pin 24 by providing additional surface contact area between the terminal pin 24 and the fixation tool 100. Additionally or alternatively, the surface of the insert slot 120 may be textured to provide additional surface contact area between the terminal pin 24 and the fixation tool 100.

The insert 112 is illustrated as having a circular shape. However, it is understood that in other embodiments, the insert 112 may have a shape that is a square, a triangle, or other polygon.

Figure 3A:
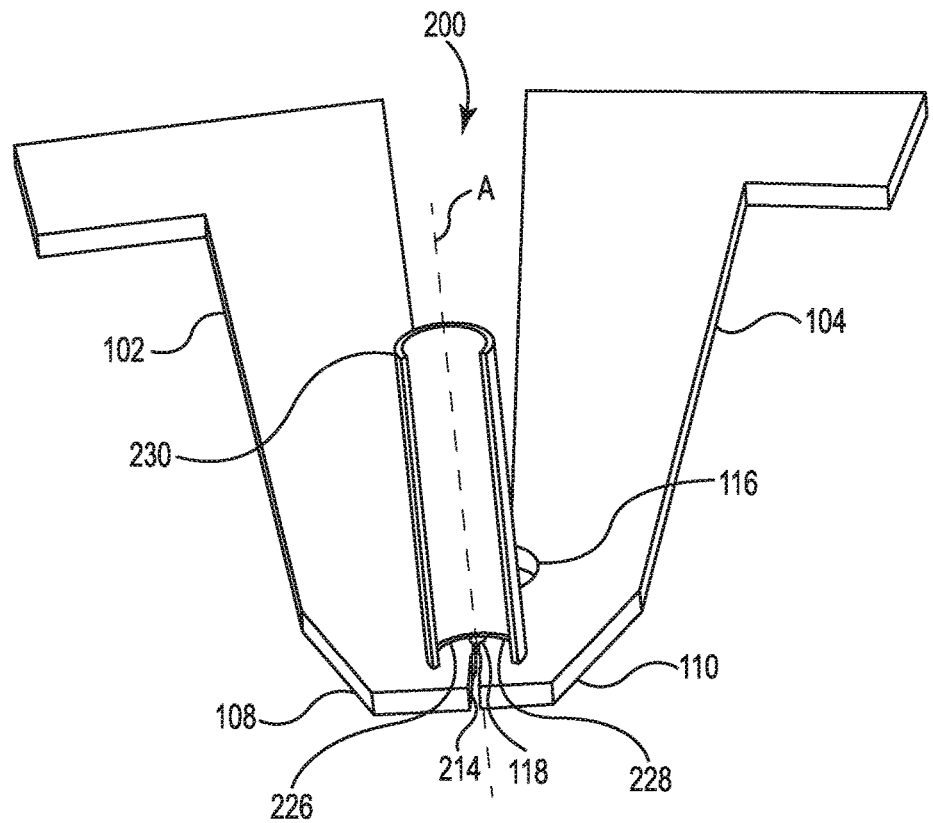
FIGS. 3A and 3B are perspective views of another exemplary fixation tool.
Figure 3B:
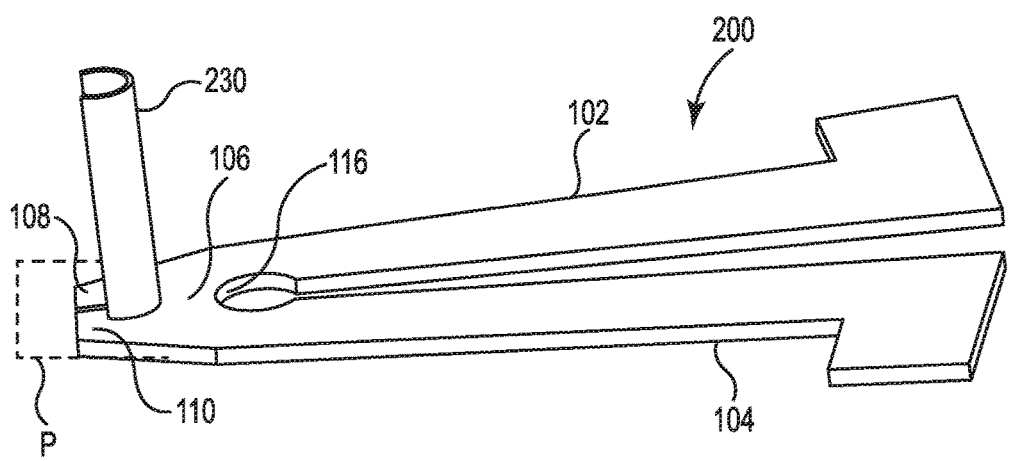

FIGS. 3A and 3B are perspective views of another exemplary fixation tool. FIG. 3A is a jaw-end view of a fixation tool 200. FIG. 3B is a side view of the fixation tool 200. The fixation tool 200 is similar to the fixation tool 100 described above, except that the fixation tool 200 as illustrated in FIGS. 3A and 3B includes a lead support member 230. The fixation tool 200 is illustrated without the insert 112 for clarity. The tool slot 214 is similar to the tool slot 114, but has no provision for the insert 112. However, it is understood that embodiments of the present invention may include fixation tool 200 as described herein and including the insert 112.

In some embodiments, the lead support member 230 may be a tube-shaped structure having a cross-section in the form of a circle. In the embodiment shown in FIGS. 3A and 3B, the lead support member 230 is an "open-tube" or trough-like structure having a cross-section in the form of a major arc of a circle defining an axis A. That is, the cross-section is more than a semicircle. In some embodiments, the major arc is greater than 180 degrees. In other embodiments, the major arc is greater than 180 degrees and less than about 220 degrees.

As shown in FIGS. 3A and 3B, in some embodiments the lead support member 230 may project from at least one of the first jaw 108 and the second jaw 110. For example, in some embodiments, the lead support member 230 may be physically attached to the first jaw 108 at a first interface 226, and be adjacent to the second jaw 110, but not physically attached to the second jaw 110. In other embodiments, the lead support member 230 may be physically attached to the first jaw 108 at the first interface 226, and physically attached to the second jaw 110 at a second interface 228. In some embodiments, the lead support member 230 may be physically attached to the first jaw 108 at the first interface 226 and/or to the second jaw 110 at the second interface 228 by, for example, gluing, laser welding or radio frequency welding. In other embodiments the lead support member 230 may also be physically attached by providing the lead support member 230 with suitable structures interfacing with, for example, the jaw stress relieving element 118 to permit snapping the lead support member 230 into place.

As shown in FIGS. 3A and 3B, the lead support member 230 may project perpendicularly from the fixation tool 200. That is, the lead support member 230 may project from the at least one of the first jaw 108 and the second jaw 110 in a direction perpendicular to a plane P containing the movement of the first jaw 108 and the second jaw 110. The lead support member 230 is disposed such that the axis A of the lead support member 230 is aligned with the tool slot 214.

Figure 4:
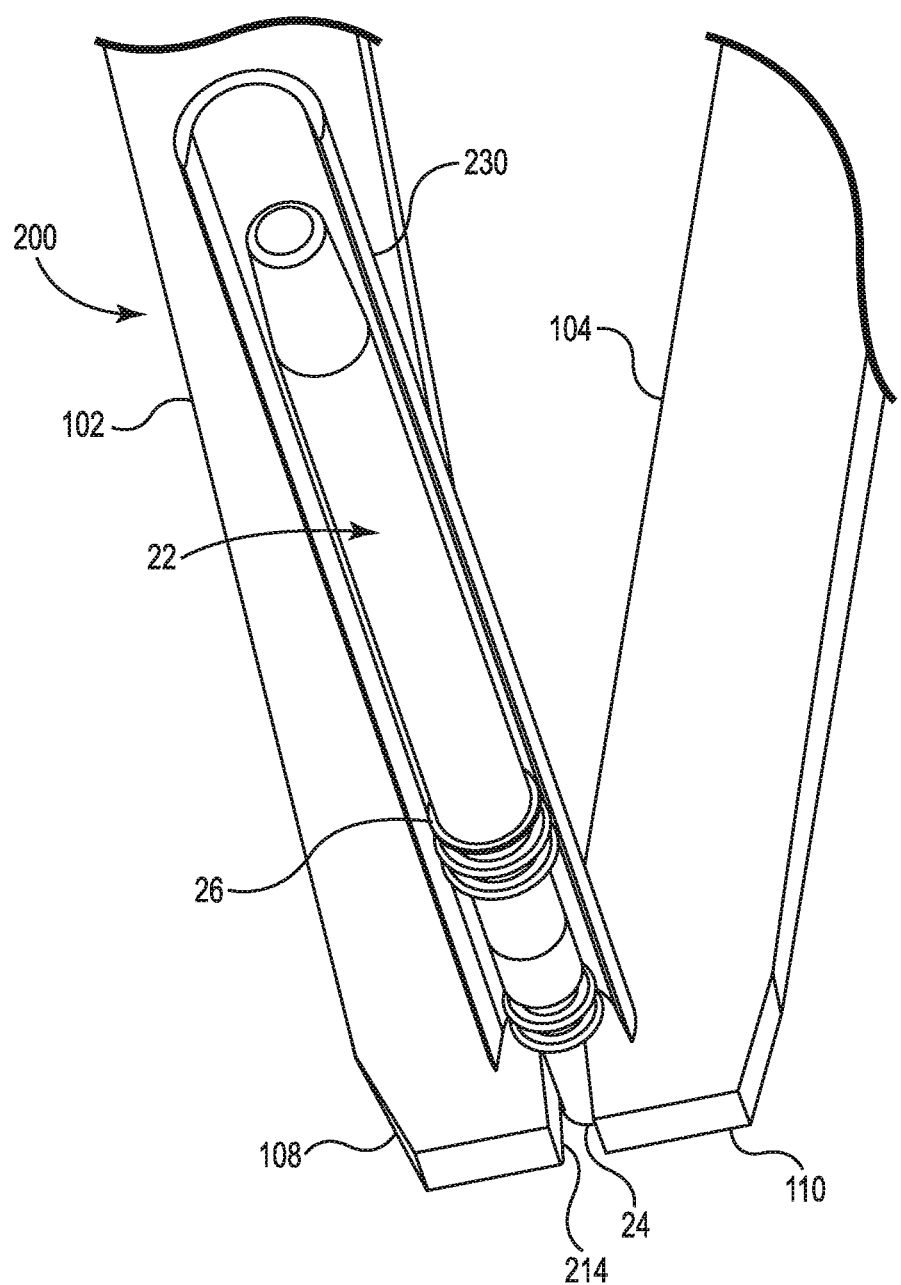
FIG. 4 is a perspective view of the fixation tool of FIGS. 3A and 3B engaging a terminal pin.

FIG. 4 is a perspective view of the fixation tool 200 of FIGS. 3A and 3B engaging the terminal pin 24 of the lead 10 as described above in reference to FIG. 1. The lead support member 230 illustrated in FIG. 4 appears to have a cross-section that is less than 180 degrees because it is shown with part of the major arc removed so that the interaction between the fixation tool 200 and the terminal boot 22 may be more clearly shown. For clarity, the lead 10 is also shown without the lead body 16 which would normally extend from the terminal boot 22.

Considering FIGS. 3A, 3B, and 4 together, the fixation tool 200 may be employed to apply torque to the terminal pin 24 while supporting the terminal boot 22 of the lead 10. The first handle 102 and the second handle 104 may be pressed toward each other. Movement of the first handle 102 and the second handle 104 works against the restoring force of the elastic member 106 moving the first jaw 108 and the second jaw 110 apart, increasing the width of the tool slot 214 from less than the diameter of the terminal pin 24 to greater than the diameter of the terminal pin 24. For embodiments in which the lead support member 230 has a cross-section forming a major arc less than about 220 degrees, once the tool slot 214 has a width greater than the diameter of the terminal pin 24, the terminal pin 24 may be slid into and along the tool slot 214 while the terminal boot 22 is snapped into place within the lead support member 230. Alternatively, for embodiments in which the lead support member 230 has a cross-section forming a circle, once the tool slot 214 has a width greater than the diameter of the terminal pin 24, the terminal boot 22 may be inserted into an open end of the lead support member 230 and toward the first jaw 108 and the second jaw 110 until the terminal pin 24 is disposed into the tool slot 214.

Releasing the first handle 102 and the second handle 104 allows the restoring force of the elastic member 106 to move the first jaw 108 and the second jaw 110 closer together, decreasing the width of the tool slot 214 to approximately the diameter of the terminal pin 24. Because the width of the tool slot 214 cannot return to the original width of less than the diameter of the terminal pin 24, sufficient restoring force of the elastic member 106 remains to secure the fixation tool 200 to the terminal pin 24. Once secured to the terminal pin 24, the fixation tool 200 may be employed to apply torque to the terminal pin 24. While torque is applied to the terminal pin 24, the terminal boot 22 may be protected and supported by the lead support member 230 and prevent or limit bending of the terminal boot 22. Without the lead support member 230, the sensitive connections between the terminal pin 24 and the electrical conductor coil contained within the terminal boot 22 may be damaged by over-bending of the terminal boot 22 during the application of torque to the terminal pin 24. In addition, squeezing the terminal boot 22 too tightly may inhibit the delivery of torque from the terminal pin 24 to the helix 20 (see FIG. 1). The lead support member 230 prevents squeezing of the terminal boot 22 during the application of torque to the terminal pin 24.

Figure 5:
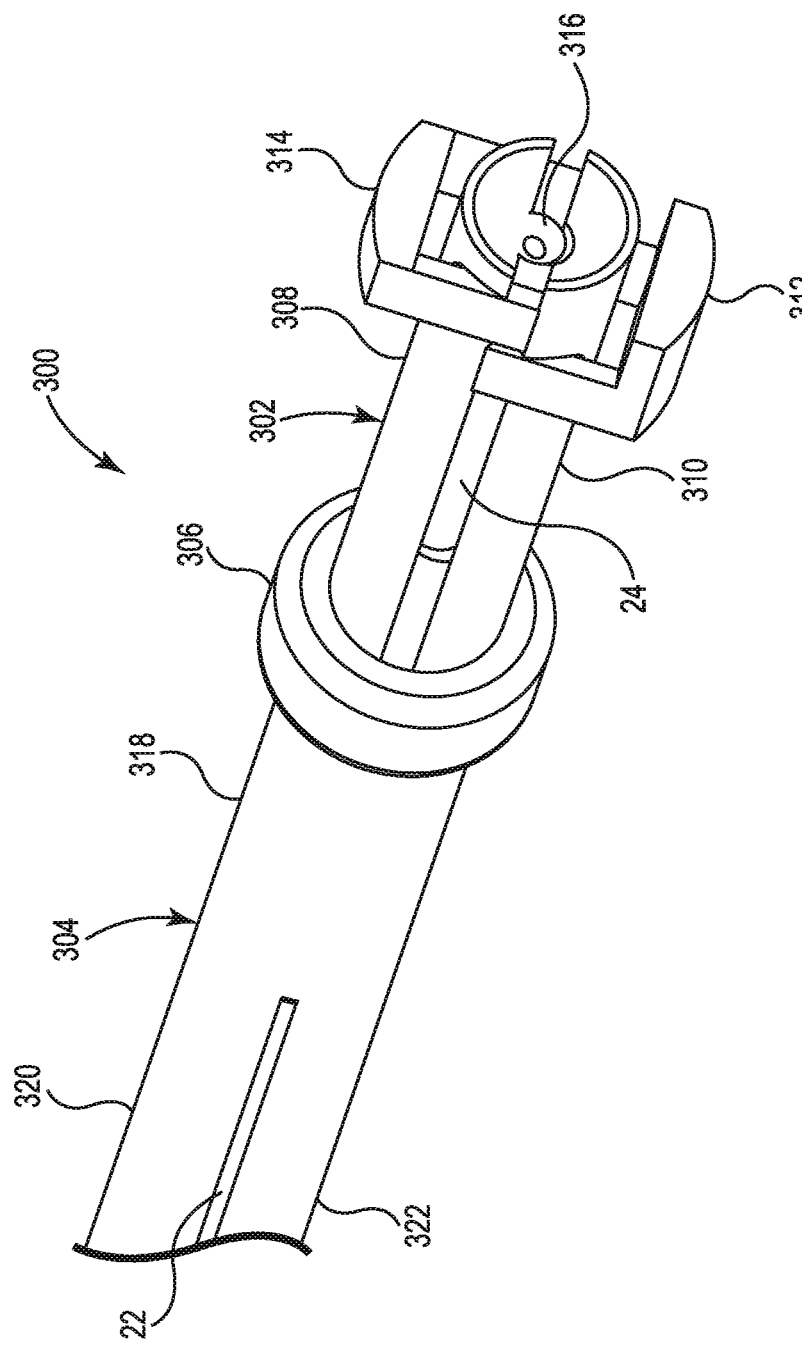
FIG. 5 is a perspective view of another exemplary fixation tool.

FIGS. 5-9 illustrate a fixation tool 300 which may be useful, for example, in applying torque to the terminal pin 24 under conditions where there may be limited clearance around the terminal boot 22. FIG. 5 is a perspective view of the fixation tool 300 with the terminal boot 22 inserted such that the terminal pin 24 is secured to the fixation tool 300 so that torque may be applied. As shown in the embodiment of FIG. 5, the fixation tool 300 may include a terminal pin member 302 and a terminal boot member 304. The terminal pin member 302 may include a first rotating joint member 306, a first jaw 308, a second jaw 310, a first tab 312, and a second tab 314. In some embodiments, the terminal pin member 302 may further include a stylet funnel 316. The first jaw 308 and the second jaw 310 may project from the first rotating member 306. The first tab 312 may be connected to the first jaw 308 and extend around the second jaw 310. Similarly, the second tab 314 may be connected to the second jaw 310 and extend around the first jaw 308. Both the first tab 312 and the second tab 314 may be distal from the first rotating joint member 306. The terminal boot member 304 may have a generally hollow, cylindrical shape and may include a second rotating joint member 318, a first leg 320, and a second leg 322. The first leg 320 and the second leg 322 may project from the second rotating joint member 318. The first rotating joint member 306 may be connected to the second rotating joint member 318 such that the terminal pin member 302 and the terminal boot member 304 may rotate freely relative to each other, as describe below in reference to FIG. 6.

The fixation tool 300 may be employed to apply torque to the terminal pin 24 while supporting the terminal boot 22 of the lead 10. The terminal boot 22 may be inserted into an end of the terminal boot member 304 distal from the second rotation member 318 (see FIG. 6). The first tab 312 and the second tab 314 may be pressed toward each other to force the first jaw 308 and the second jaw 310 apart from each other. Bending the first jaw 308 and the second jaw 310 in this way builds up a restoring force in each from the elastic nature of the material making up the terminal pin member 302. This movement also creates space for the terminal pin 24 to be inserted into the terminal pin member 302, as described below in reference to FIGS. 7A and 7B, once the terminal boot 22 is inserted fully into the terminal boot member 304.

Releasing the first tab 312 and the second tab 314 allows the restoring force built up in the first jaw 308 and the second jaw 310 to move the first jaw 308 and the second jaw 310 closer together to secure the fixation tool 300 to the terminal pin 24. The first jaw 308 and the second jaw 310 are necessarily held apart to some extent by the presence of the terminal pin 24. This may be visible as a gap between the second jaw 310 and the stylet funnel 316 as shown in FIG. 5. Once secured to the terminal pin 24, the fixation tool 300 may be employed to apply torque to the terminal pin 24. While torque is applied to the terminal pin 24, the first leg 320 and the second leg 322 may be forced together to grip at least some of the terminal boot seals 26 (see FIG. 1) to hold the terminal boot 22 securely. In this way, torque may be applied to the terminal pin 24 under conditions where there may be limited clearance around the terminal boot 22.

Figure 6:
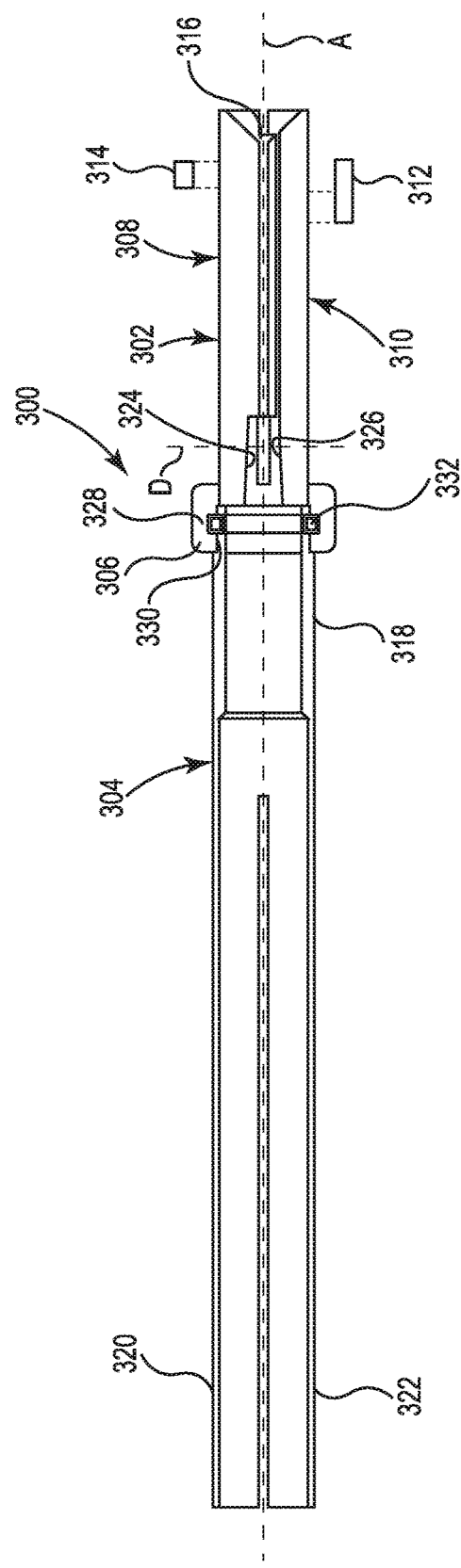
FIG. 6 is a side cross-sectional view of the fixation tool of FIG. 5.

FIG. 6 is a side cross-sectional view of the fixation tool 300. As shown in FIG. 6, the first rotating joint member 306 has a generally cylindrical shape defining a tool axis A. The first rotating joint member 306 may have a radially inward facing groove 328 and the second rotating joint member 318 may have a radially outward facing groove 330 to accommodate a C-clip 332 to connect the first rotating joint member 306 to the second rotating joint member 318. So connected, the terminal pin member 302 and the terminal boot member 304 may rotate freely with respect to each other. In the embodiment shown in FIG. 6, the second rotating joint member 318 is configured to be partially inserted into the first rotating joint member 306. However, it is understood that embodiments may also include an alternative in which the groove directions are reversed and the first rotating joint member 306 is configured to be partially inserted into the second rotating joint member 318. As shown in FIG. 6, the first leg 320 and the second leg 322 project from the second rotating joint 318 and are separated by a gap. Pressing the first leg 320 and the second leg 322 together builds up a restoring force in each from the elastic nature of the material making up the first leg 320 and the second leg 322. Releasing the first leg 320 and the second leg 322 allows the restoring force to restore the first leg 320 and the second leg 322 to their neutral positions as shown in FIG. 6.

As shown in FIG. 6, the first jaw 308 may include a first inner surface 324 facing the tool axis A. The first inner surface 324 may extend from proximate the first rotating joint member 306 to at least a distance D distal from the first rotating joint member 306. The second jaw 310 may include a second inner surface 326 facing the tool axis A. The second inner surface 326 may extend from proximate to the first rotating joint member 306 to at least the distance D distal from the first rotation join member 306.

FIGS. 7A and 7B are side cross-sectional views of the terminal pin member 302 illustrating additional details. As shown in a relaxed state in FIG. 7A, the second inner surface 326 may be disposed diametrically opposite of the first inner surface 324. The first inner surface 324 and the second inner surface 326 may be diametrically spaced from each other by a first width proximate to the first rotating joint member 306, and by a second width at the distance D distal from the first rotating joint member 306 in which the second width is less than the first width. That is, for example, in embodiments where the first inner surface 324 and the second inner surface 326 have axial cross-sections that are arcs of a circle, the diametrical space is the distance between any point on the first inner surface 324 and a point on the second inner surface 326 that is in the same axial plane and in a line with the point on the first inner surface 324 and the tool axis A. Thus, the first inner surface 324 and the second inner surface 326 taper toward each other away from the first rotating joint member 306. In some embodiments, the first width may be greater than or equal to the diameter of terminal pin 24 (see FIG. 1).

FIG. 7B shows the terminal pin member 302 in a state where the first jaw 308 and the second jaw 310 are elastically bent by pressing the first tab 312 and the second tab 314 together. As shown in FIG. 7B, pressing the first tab 312 and the second tab 314 together forces the first jaw 308 and the second jaw 310 away from each other such that the first inner surface 324 and the second inner surface 326 are spaced from each other by at least the first width at the distance D distal from the first rotating joint member 306. In embodiments where the first width is greater than or equal to the diameter of the terminal pin 24 (FIG. 1), forcing the first jaw 308 and the second jaw 310 apart in this way allows the terminal pin 24 to be inserted into the terminal pin portion 302 at least up to the distance D.

FIG. 7B also shows that the stylet funnel 316 may extend along at least a portion of the first jaw 308. As shown in FIG. 7A, once returned to a relaxed state, the stylet funnel 316 may be coaxial with the tool axis A.

FIG. 8 is a side cross-sectional view of the terminal boot member 304 to illustrate details that may not be clear in other figures illustrating the terminal boot member 304, such as the radially outward facing groove 330. As shown in FIG. 8, the first leg 320 and the second leg 322 project from the second rotating joint 318 and are separated by a gap allowing them to be pressed together. In a relaxed state, the second leg 322 is spaced diametrically apart from the first leg 320 by a third width. Pressing the first leg 320 and the second leg 322 together spaces the second leg 322 diametrically apart from the first leg 320 by a fourth width, which is less than the third width. Considering FIGS. 1 and 8 together, in some embodiments, the third width is greater than a diameter of the terminal boot seal 26 and the fourth width is less than the diameter of the terminal boot seal 26. In such embodiments, the terminal boot 22 may be inserted into the terminal boot member 304 without interference.

Figure 9:
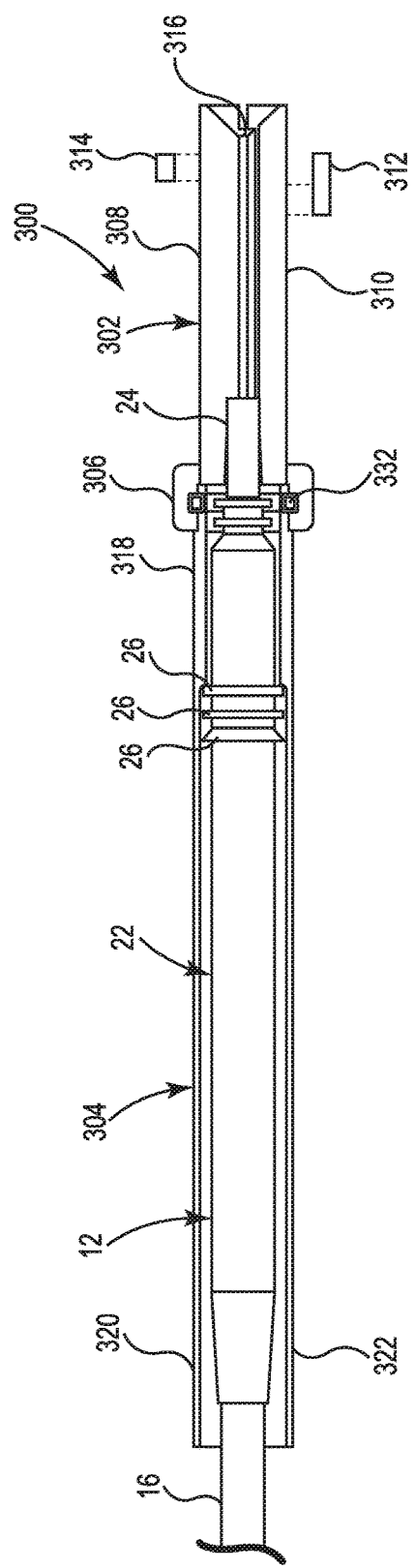
FIG. 9 is a combined side cross-sectional and side view of the fixation tool of FIG. 5 engaging a terminal boot and a terminal pin.

FIG. 9 is a combined side cross-sectional and side view of the fixation tool 300 engaging the terminal boot 22 and the terminal pin 24. As shown in FIG. 9, the terminal pin member 302 is secured to the terminal pin 24 as described above in reference to FIGS. 5-7B. While not visible on the scale of FIG. 9, the first jaw 308 and the second jaw 310 are held apart slightly by the presence of the terminal pin 24 (see FIG. 5). During the application of torque to the terminal pin 24, the first leg 320 and the second leg 322 may be pressed together to provide a secure grip on the terminal boot 22 without bending it and without squeezing so hard that it interferes with the delivery of torque from the terminal pin 24 to the helix 20 (see FIG. 1).

The terminal pin member 302 and the terminal boot member 304 may each be integrally molded of any strong, elastic material, for example, a hard plastic, such as ABS or polycarbonate.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A fixation tool for applying torque to a terminal pin of an active fixation medical electrical lead, the tool comprising:
    a first handle;
    a second handle;
    an elastic member connecting the first handle to the second handle;
    a first jaw projecting beyond the elastic member from the first handle;
    a second jaw projecting beyond the elastic member from the second handle, wherein the first jaw and the second jaw are spaced apart, forming a tool slot extending from ends of each of the first jaw and the second jaw distal from the elastic member and toward the elastic member; and
    an insert disposed at an end of the tool slot distal to the elastic member, the insert including an insert slot configured to align with the tool slot, the tool configured such that pressing the first handle and the second handle toward each other causes a movement of the first jaw and the second jaw relative to each other to change a width of the insert slot,
    wherein the first jaw and the second jaw are comprised of a first material, the insert is comprised of a second material, and the first material is harder than the second material; wherein the tool is configured such that pressing the first handle toward the second handle causes a movement of the first jaw and the second jaw away from each other, increasing a width of the insert slot from less than a diameter of the terminal pin to greater than the diameter of the terminal pin.

2. The tool of claim 1, wherein the first handle, the second handle, the elastic member, the first jaw and the second jaw are integrally formed.

3. The tool of claim 2, wherein the insert is disposed in the tool by insert molding.

4. The tool of claim 1, wherein the second material has a Shore hardness of less than 90 D.

5. The tool of claim 4, wherein the second material is silicone rubber and the insert is glued to the first jaw and the second jaw.

6. The tool of claim 1, wherein the insert includes a plurality of structures projecting from a surface of the insert slot.

* * * * *